United States Patent
Liu et al.

(10) Patent No.: US 8,003,755 B2
(45) Date of Patent: *Aug. 23, 2011

(54) HYDROCHLORIDE SALTS OF A GLYCOPEPTIDE PHOSPHONATE DERIVATIVE

(75) Inventors: Jyanwei Liu, Sunnyvale, CA (US); Junning Lee, El Granada, CA (US)

(73) Assignee: Thervance, Inc., South San Francisco, CA (US)

(*) Notice: Subject to any disclaimer, the term of this patent is extended or adjusted under 35 U.S.C. 154(b) by 762 days.

This patent is subject to a terminal disclaimer.

(21) Appl. No.: 12/082,096

(22) Filed: Apr. 8, 2008

(65) Prior Publication Data

US 2009/0069534 A1 Mar. 12, 2009

Related U.S. Application Data

(63) Continuation of application No. 10/970,128, filed on Oct. 21, 2004, now Pat. No. 7,531,623.

(60) Provisional application No. 60/513,359, filed on Oct. 22, 2003.

(51) Int. Cl.
*C07K 5/037* (2006.01)
(52) U.S. Cl. .................................. 530/323; 530/317
(58) Field of Classification Search ............. 530/317
See application file for complete search history.

(56) References Cited

U.S. PATENT DOCUMENTS

| 3,067,099 | A | 12/1962 | McCormick et al. |
| 4,885,275 | A | 12/1989 | Robison |
| 6,391,851 | B1 | 5/2002 | Sawai et al. |
| 6,635,618 | B2 | 10/2003 | Leadbetter et al. |
| 6,858,584 | B2 | 2/2005 | Judice et al. |
| 6,872,701 | B2 | 3/2005 | Leadbetter et al. |
| 6,887,976 | B2 | 5/2005 | Leadbetter et al. |
| 6,979,723 | B2 | 12/2005 | Leadbetter et al. |
| 7,015,305 | B2 | 3/2006 | Lee et al. |
| 7,015,307 | B2 | 3/2006 | Schmidt et al. |
| 7,208,471 | B2 | 4/2007 | Leadbetter |
| 7,351,691 | B2 | 4/2008 | Leadbetter et al. |
| 7,531,623 | B2 | 5/2009 | Liu et al. |

FOREIGN PATENT DOCUMENTS

| WO | 03/018608 A2 | 3/2003 |
| WO | 03/029270 A2 | 4/2003 |

OTHER PUBLICATIONS

Diana et al., "Development and validation of an improved method for the analysis of vancomycin by liquid chromatography; Selectivity of reversed-phase columns towards vancomycin components", Journal of Chromatography A, 996, pp. 115-131 (2003).

"Telavancin Hydrochloride", Drugs of the Future 2004, 29(12): pp. 1211-1219 (2004).

*Primary Examiner* — Bernard Dentz
(74) *Attorney, Agent, or Firm* — Jeffrey A. Hagenah

(57) ABSTRACT

Disclosed are hydrochloride salts of telavancin having a chloride ion content of from about 2.4 wt. % to about 4.8 wt. %. The disclosed salts have improved stability during storage at ambient temperatures compared to other hydrochloride salts. Also disclosed are processes for preparing such salts.

5 Claims, 2 Drawing Sheets

HYDROCHLORIDE SALTS OF A GLYCOPEPTIDE PHOSPHONATE DERIVATIVE

CROSS-REFERENCE TO RELATED APPLICATIONS

This application is a continuation of U.S. application Ser. No. 10/970,128, filed Oct. 21, 2004 now U.S. Pat. No. 7,531,623; which application claims the benefit under 35 U.S.C. §119(e) of U.S. Provisional Application No. 60/513,359, filed Oct. 22, 2003, the disclosures of which are incorporated herein by reference in their entirety.

BACKGROUND OF THE INVENTION

1. Field of the Invention

The invention is directed to hydrochloride salts of a phosphonate derivative of a glycopeptide antibiotic, which salts are useful for formulating pharmaceutical compositions containing the antibiotic agent. The invention is also directed to processes for preparing such salts.

2. Background

Glycopeptides (e.g. dalbaheptides) are a well-known class of antibiotics produced by various microorganisms (see *Glycopeptide Antibiotics*, edited by R. Nagarajan, Marcel Dekker, Inc. New York (1994)). These complex multi-ring peptide compounds are very effective antibacterial agents against a majority of Gram-positive bacteria.

Commonly assigned U.S. Pat. No. 6,635,618, incorporated herein by reference in its entirety, discloses a novel class of glycopeptide phosphonate derivatives that are potent antibiotic agents having effective antibacterial activity against a wide range of Gram-positive bacteria.

Specifically, this application discloses a compound of formula 1:

This compound is known in the art as telavancin.

To efficiently use telavancin in the preparation of pharmaceutical compositions and formulations, it would be highly desirable to have salt forms that have improved stability during storage at ambient temperatures. No such salt forms have been disclosed previously.

SUMMARY OF THE INVENTION

The present invention provides hydrochloride salts of telavancin having a chloride ion content of from about 2.4 wt. % to about 4.8 wt. %. Surprisingly, such hydrochloride salts have been found to have improved stability during storage at ambient temperatures compared to other hydrochloride salts of telavancin.

Accordingly, in one embodiment, this invention is directed to a hydrochloride salt of telavancin having a chloride ion content of from about 2.4 wt. % to about 4.8 wt. %.

In another aspect, the present invention is directed to a process for preparing a hydrochloride salt of telavancin having a chloride ion content of from about 2.4 wt. % to about 4.8 wt. %; the process comprising the steps of:

(a) providing a composition comprising a hydrochloride salt of telavancin having a chloride ion content greater than about 4.8 wt. % and an aqueous solvent system, wherein the composition has a pH of less than or equal to about 2.0;

(b) adjusting the pH of the composition to from about 2.5 to about 5.0 to form a hydrochloride salt of telavancin having a chloride ion content of from about 2.4 wt. % to about 4.8 wt. %; and (c) isolating the hydrochloride salt of telavancin produced in step (b).

In yet another embodiment, this invention is directed to a composition comprising a hydrochloride salt of telavancin

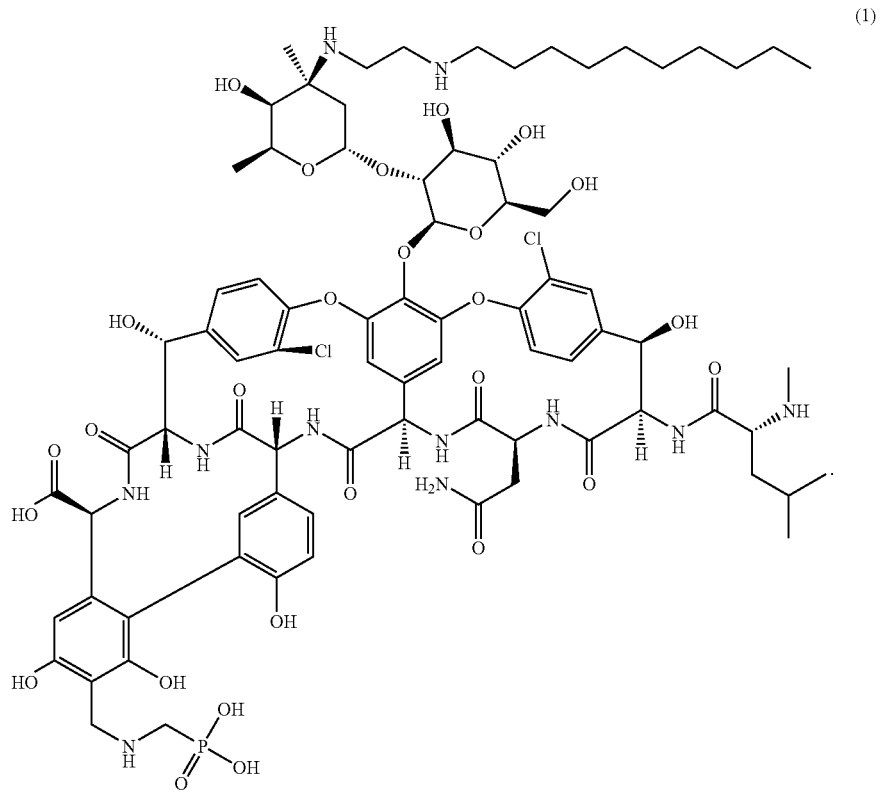

(1)

and an aqueous solvent system wherein the pH of the composition ranges from about 2.5 to about 5.0.

DETAILED DESCRIPTION OF THE INVENTION

Figure 1:
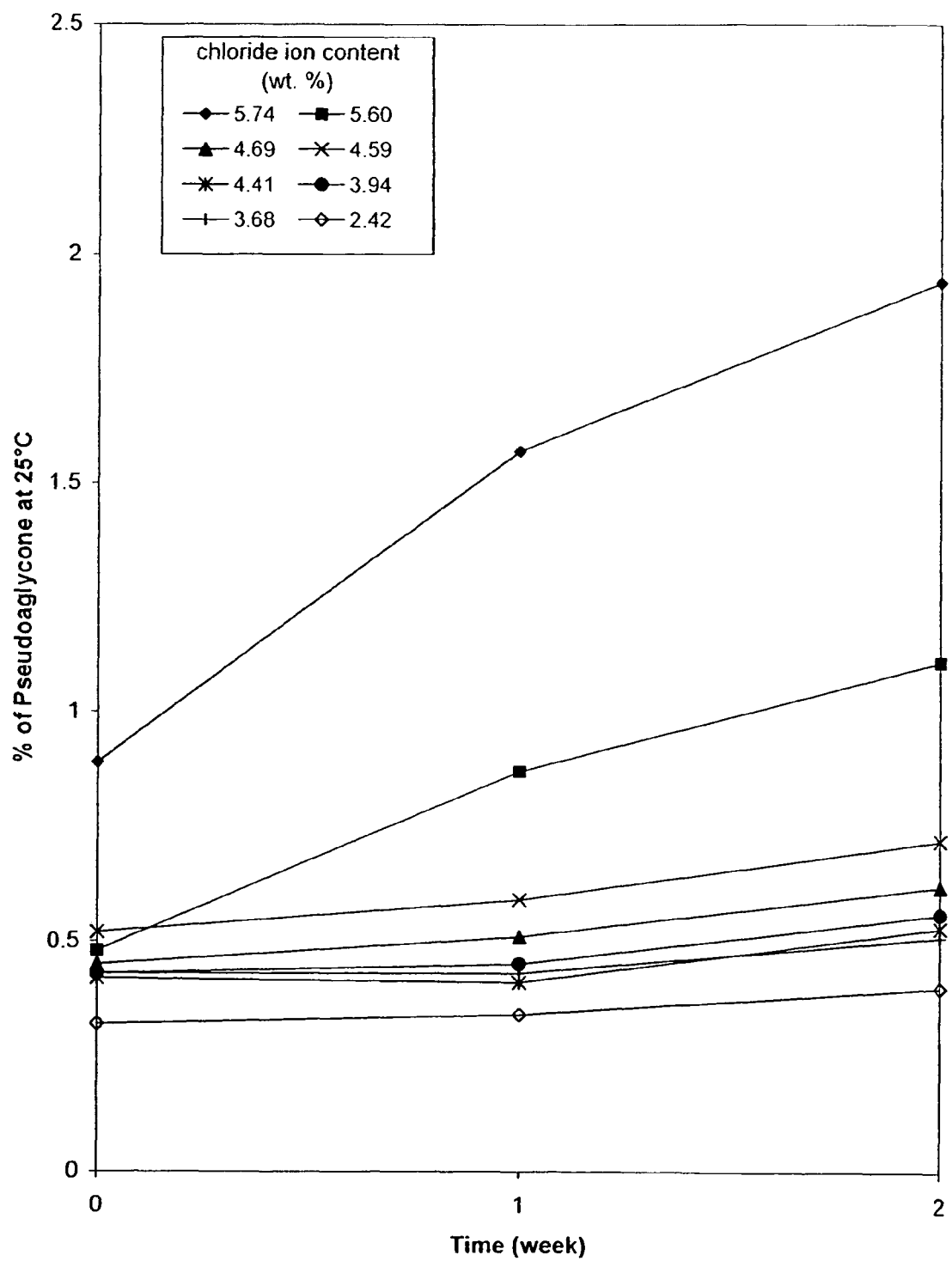
FIG. 1 is a graph showing the HPLC area percent of pseudoaglycone present in eight samples of hydrochloride salts of telavancin vs. time when the samples are stored at 25° C.

This invention is directed to certain hydrochloride salts of telavancin that have improved stability upon storage at ambient temperatures. Such salts are useful for preparing pharmaceutical compositions and formulations.

In describing the invention, the following terms have the following meanings, unless otherwise indicated.

As used herein the term "hydrochloride salt" or "hydrochloride" refers to a salt prepared from the reaction of hydrochloric acid and the compound of interest, i.e., telavancin. Unless explicitly stated, no particular stoichiometry is implied by the use of this term.

The term "chloride ion content" refers to the weight percent (wt. %) of chloride ions present in a sample of the compound of interest in its hydrochloride salt form. This term does not include the weight of any covalently bound chloro substituents present in the compound of interest, i.e., the chloro substituents on the aromatic rings (rings C and E) of telavancin. Thus, the term "chloride ion content" refers to the non-covalently bound chloride ion content of a sample. When used to describe the compounds of this invention, the chloride ion content is calculated based on an essentially anhydrous weight of the sample, i.e., with water content of the sample deducted from the total weight of the sample.

As used herein, the terms "inert solvent" and "inert diluent" refer to a solvent or diluent which is essentially inert under the conditions of the reaction in which it is employed as a solvent or diluent.

The term "aqueous solvent system" refers to a solution comprising water and at least one inert organic solvent or inert organic diluent.

Where a range of values is provided, it is understood that each intervening value, to the tenth of the unit of the lower limit unless the content clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

In one aspect, the invention is directed to a hydrochloride salt of telavancin having a chloride ion content of from about 2.4 wt. % to about 4.8 wt. %.

In another aspect, the invention is directed to a hydrochloride salt of telavancin having a chloride ion content of from about 2.4 wt. % to about 4.7 wt. %; including from about 2.4 wt. % to about 4.6 wt. %.

In another aspect, the invention is directed to a hydrochloride salt of telavancin having a chloride ion content of from about 3.7 wt. % to about 4.6 wt. %; including from about 3.7 wt. % to about 4.4 wt. %; such as, for example, from about 3.9 wt. % to about 4.4 wt. % or from about 3.7 wt. % to about 3.9 wt. %.

The weight percent of chloride ions present in a sample can be determined, for instance, by the method outlined in *United States Pharmacopeia* (USP) 23, section 221, page 1726 (1995), or by a number of other techniques known to one skilled in the art. For example, one common technique is potentiometric titration with silver nitrate. Another technique is based on gravimetric determination of the amount of silver chloride precipitated from a sample on addition of silver nitrate. Alternatively, any other suitable method for determining the weight percent of chloride ions present in a sample may be used.

Since the amount of water present in samples of hydrochloride salts of telavancin can vary significantly, the weight of any water present in the sample is deducted before the chloride ion content of the sample is calculated.

Additionally, the weight of sample, from which the chloride ion content is calculated, includes any impurities present in the hydrochloride salt of telavancin. The amount of impurities present in a sample of a hydrochloride salt of telavancin is typically less than about 15%, for example, less than 12%.

Thus, the chloride ion content of a sample is determined as follows:

$$\text{wt. of sample} \times \frac{(100 - \text{wt. \% of water in sample})}{100} = \text{wt. of telavancin hydrochloride}$$

$$\text{wt. of sample} \times \frac{(\text{wt. \% of chloride ion})}{100} = \text{wt. of chloride ion}$$

$$\text{chloride ion content} = \frac{\text{wt. of chloride ion}}{\text{wt. of telavancin hydrochloride}} \times 100$$

Water content is typically determined using the potentiometric Karl Fischer method as outlined in *United States Pharmacopeia* (USP) 25, section 921, pages 2085-2088 (2002) but can also be determined using other techniques known to those in the art.

For reference, a monohydrochloride salt of telavancin (molecular weight 1792.06) (0% $H_2O$) has a chloride ion content of 1.98 wt. %. Correspondingly, a dihydrochloride salt of telavancin (mol. wt. 1828.52) and a trihydrochloride salt of telavancin (mol. wt. 1864.98) have chloride ion contents of 3.88 wt. % and 5.70 wt. %, respectively.

Thus, the hydrochloride salts of the invention having a chloride ion content of from about 2.4 wt. % to about 4.8 wt. % correspond to more than about 1 and less than about 3 molar equivalents of hydrochloride per molar equivalent of telavancin. In one aspect, the invention is directed to a hydrochloride salt of telavancin having from about 1.5 to about 2.5 molar equivalents of hydrochloride per molar equivalent of telavancin. A preferred stoichiometry for the hydrochloride salts of the invention is about 2 molar equivalents of hydrochloride per molar equivalent of telavancin.

The degradation products of pharmaceutical compounds such as glycopeptides are of concern because such degradation products may differ in their biological activity or therapeutic effect compared to the parent molecule. See, for example, J. Diana et al., *Journal of Chromatography A*, 996: 115-131 (2003), which discusses vancomycin impurities.

Upon storage at ambient temperatures, certain hydrochloride salts of telavancin have been found to produce small amounts of undesirable degradation products and impurities. The two principal degradation products are (1) a pseudoaglycone impurity of telavancin; and (2) an aglycone impurity of telavancin (the structures of which are shown below). The pseudoaglycone impurity is derived from hydrolysis of the lipidated vancosamine moiety of telavancin and the aglycone impurity is derived from the hydrolysis of the glucose moiety of telavancin.

Previously disclosed processes for preparing telavancin have isolated the hydrochloride salt of telavancin from a solution having a pH of less than about 2, thereby resulting in a hydrochloride salt of telavancin having a chloride ion content greater than about 5 wt. %, i.e., providing a hydrochloride salt of telavancin that is approximately a trihydrochloride salt of telavancin. A sample lot of such salts, after drying at 20-30° C. for two days, contained a combined total of about 8% of the pseudoaglycone and aglycone degredation byproducts. Upon storage of hydrochloride salts of telavancin having a chloride

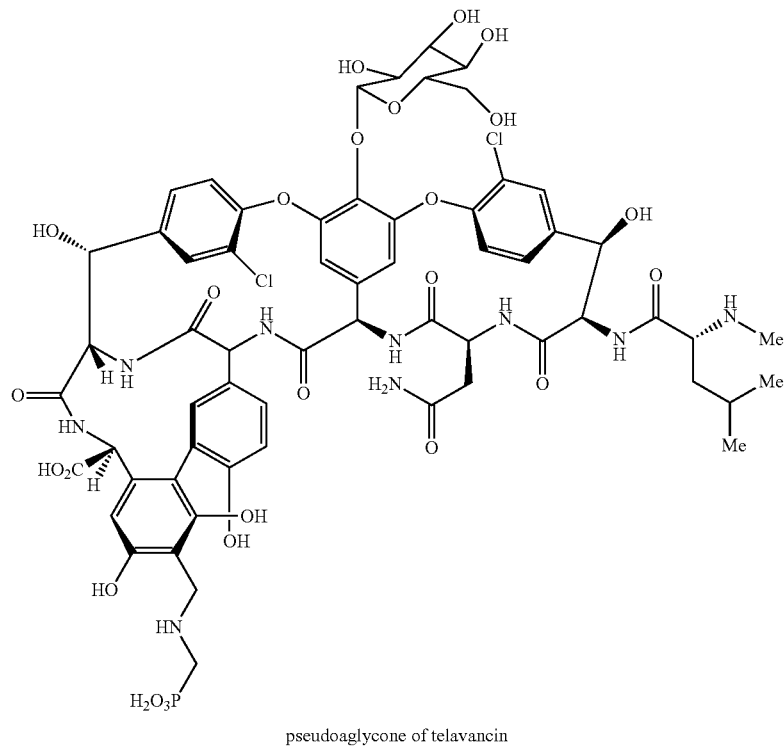

pseudoaglycone of telavancin

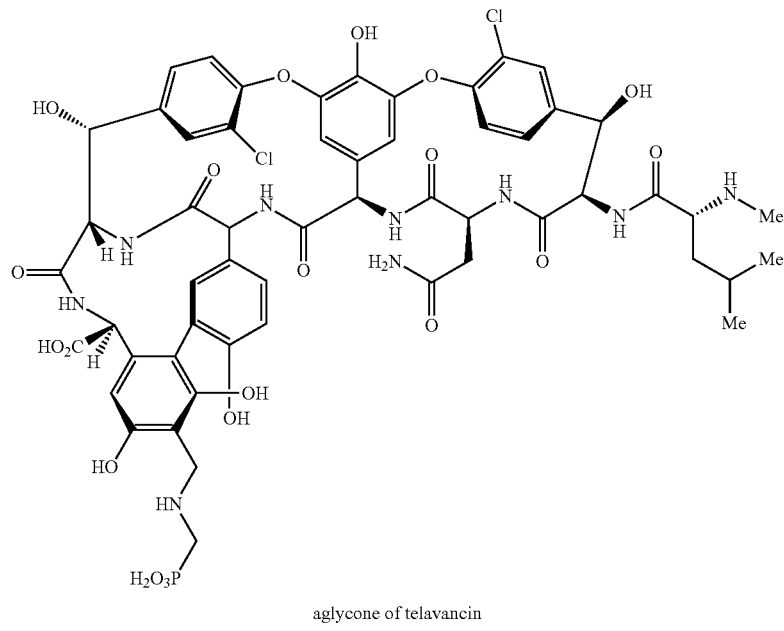

aglycone of telavancin ion content of greater than about 5 wt. % at 25° C. for 2 weeks under controlled conditions, an increase of more than 0.6% pseudoaglycone and 0.4% aglycone was observed.

In contrast, under similar conditions, hydrochloride salts of telavancin having a chloride ion content of from about 2.4 wt. % to about 4.8 wt. % demonstrated an increase of less than 0.2% pseudoaglycone and less than 0.07% aglycone impurities. Thus, the amounts of psuedoaglycone and aglycone impurities produced upon storage of the salts of this invention at ambient temperatures are significantly less than those produced by previously disclosed hydrochloride salts.

In a second embodiment, the invention is directed to a process of preparing a hydrochloride salt of telavancin having a chloride ion content of from about 2.4 wt. % to about 4.8 wt. %. The process includes providing a composition comprising a hydrochloride salt of telavancin having a chloride ion content greater than about 4.8 wt. % in a first step (a) and adjusting the pH of the composition in a second step (b).

The process of the invention can use a solution obtained directly from the general synthesis scheme described herein of a hydrochloride salt of telavancin or the composition can be formed by redissolving an isolated hydrochloride salt of telavancin. Accordingly, in one aspect of the invention, the composition of step (a) is obtained directly from the synthesis process of a hydrochloride salt of telavancin. In another aspect of the invention, an isolated hydrochloride salt of telavancin having a chloride ion content greater than 4.8 wt. % is redissolved to comprise the composition of step (a). For example, a lyophilized hydrochloride salt of telavancin having a chloride ion content greater than 4.8 wt. % can be redissolved to comprise the composition of step (a).

In step (a) of the above process, the composition comprises a hydrochloride salt of telavancin and an aqueous solvent system, wherein the composition has a pH of less than or equal to about 2.0. The aqueous solvent system employed in step (a) typically comprises water and at least one organic diluent. Organic diluents suitable for use in combination with water are those that are: (1) miscible with water; and (2) chemically inert to a hydrochloride salt of telavancin. Useful organic diluents include acetonitrile, methanol, ethanol, propanol, isopropanol, tert-butanol, dioxane, and the like. For example, the organic diluent can be selected from the group consisting of acetonitrile, methanol, and ethanol. In a particular example, the composition of step (a) comprises acetonitrile and water. Of particular interest is when the aqueous solvent system of step (a) is a solution of from about 40% to about 60% (v/v) acetonitrile to water.

The preferred concentration of the hydrochloride salt of telavancin in the composition of step (a) is from about 5 mg/mL to about 30 mg/mL. For instance, the concentration of the hydrochloride salt of telavancin can be from about 20 mg/mL to about 30 mg/mL in the initial composition of step (a).

In step (b) of the invention, the pH of the composition is adjusted to a range of from about 2.5 to about 5.0. In one aspect, in step (b) of the process, the pH of the composition is adjusted to a range of from about 3.0 to about 5.0. For example, in step (b), the pH of the composition can be adjusted to a range of from about 3.0 to about 4.5, such as from about 3.0 to about 4.0. In step (b), the pH of the composition can be adjusted to a range of from about 3.5 to about 4.5. For instance, the pH of the composition can be adjusted to a range of from about 3.5 to about 4.0. In one aspect, the pH of the composition is adjusted to a range of from about 4.0 to about 4.5.

In step (b), the pH of the composition is typically adjusted by the dropwise addition of an alkali hydroxide to the composition of step (a). Any suitable alkali hydroxide may be used, including by way of example, barium hydroxide, sodium hydroxide, potassium hydroxide, lithium hydroxide, and the like. Of particular interest is the use of sodium hydroxide to adjust the pH of the composition.

Finally, in a third step (c), the hydrochloride salt of telavancin is isolated from the composition of step (b) by any of a number of methods known in the art. For example, the hydrochloride salt of telavancin can be precipitated and centrifuged or filtered.

In one aspect of the invention, in step (c), the hydrochloride salt of telavancin is isolated from the composition by precipitation and filtration. For example, an excess of an organic diluent can be used to precipitate the hydrochloride salt of telavancin out of the composition. Suitable organic diluents to be used in step (c) to precipitate the hydrochloride salt of telavancin from the composition of step (b) are those that are: (1) miscible with water; (2) chemically inert to a hydrochloride salt of telavancin; and (3) result in a precipitate of the hydrochloride salt of telavancin when added to the composition of step (b). Useful organic diluents include, by way of illustration, acetonitrile, methanol, ethanol, acetone, and the like. In one aspect of the invention, in step (c), acetonitrile is added to the composition of step (b) to precipitate the hydrochloride salt of telavancin. In another aspect of the invention, acetone is added to the composition of step (b) to precipitate the hydrochloride salt of telavancin.

If desired, the precipitate isolated in step (c) can optionally be washed with a suitable organic diluent. For example, when acetonitrile is added to the composition of step (b) to precipitate the hydrochloride salt of telavancin, the resulting precipitate is optionally washed with acetonitrile followed by methyl tert-butyl ether (MTBE). Alternatively, when acetone is used to precipitate the hydrochloride salt of telavancin, the resulting precipitate is optionally washed with acetone followed by MTBE.

Steps (a), (b), and (c) of the process of the invention described herein are generally conducted at an internal temperature of from about 15° C. to about 30° C., typically at a range of between about 20° C. to about 25° C.

Typically, when conducting the process of the invention, all filtration, washing, drying and sieving are done under an inert atmosphere, such as nitrogen, argon and the like.

In another embodiment, the invention is directed to a composition comprising a hydrochloride salt of telavancin and an aqueous solvent system wherein the pH value of the composition ranges from about 2.5 to about 5.0. In a further aspect of the invention, the invention is directed to said composition wherein the composition has any one of the particular pH values described herein.

Also embodied in the invention is the product prepared by any one of the processes described herein for preparing a hydrochloride salt of telavancin having a chloride ion content of from about 2.4 wt. % to about 4.8 wt. % or any of the particular chloride ion content ranges described herein.

General Synthetic Procedures

Telavancin or a salt thereof can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Additionally, as will be apparent to those skilled in the art, conventional protecting groups may be necessary to prevent certain functional groups from undergoing undesired reactions.

Detailed procedures for preparing telavancin or a salt thereof are described in U.S. patent application Ser. Nos. 10/226,988, filed on Aug. 23, 2002; 10/226,676, filed on Aug. 23, 2002; and 10/226,428, filed on Aug. 23, 2002; the disclosures of which are incorporated herein by reference in their entirety. Any of the procedures disclosed in these publications may be used to prepare telavancin or a salt thereof.

By way of illustration, vancomycin or a salt thereof, is first reductively alkylated at the vancosamine amino terminus using an N-protected-decylaminoacetaldehyde. For example, one molar equivalent of vancomycin or a salt thereof, is combined with one or more molar equivalents of an N-protected-decylaminoacetaldehyde, such as N-Fmoc-decylaminoacetaldehyde, and an excess of a suitable base in an inert diluent to form a composition. Preferably, from about 1 to about 2 molar equivalents of the aldehyde are used in this step of the process. In this composition, a mixture of imines and/or hemiaminals is believed to be formed between the aldehyde and the basic nitrogen atoms of vancomycin, i.e., the vancosamine nitrogen atom and the N-terminal (leucinyl) nitrogen atom.

Typically, the vancomycin or a salt thereof and the aldehyde are combined in an inert diluent in the presence of an excess amount of a suitable base to form a mixture. A suitable inert diluent, or combination of solvents include, for example, N,N-dimethylformamide, N,N-dimethylacetamide, N-methylpyrrolidinone, acetonitrile/water, and the like or mixtures thereof.

Any suitable base may be employed in this step to neutralize the vancomycin salt and to facilitate formation of the imine and/or hemiaminal, including organic bases, such as amines, alkali metal carboxylate salt (i.e., sodium acetate and the like) and inorganic bases, such as alkali metal carbonates (i.e., lithium carbonate, potassium carbonate and the like). Typically, the base used in this step is a tertiary amine such as, by way of illustration, triethylamine, diisopropylethylamine, N-methylmorpholine, and the like.

This first step of the process is typically conducted at a temperature ranging from about 0° C. to about 75° C., preferably at ambient temperature (i.e., about 20-25° C.) for about 1 to about 24 hours, preferably for about 6 to 12 hours, or until formation of the imine and/or hemiaminal is substantially complete.

When formation of the imine and/or hemiaminal mixture is substantially complete, the mixture is acidified with an excess of acid. Any suitable acid may be employed in this step of the process including, by way of illustration, carboxylic acids (e.g. acetic acid, trichloroacetic acid, citric acid, formic acid, trifluoroacetic acid, methanesulfonic acid, toluenesulfonic acid and the like), mineral acids (e.g. hydrochloric acid, sulfuric acid, or phosphoric acid), and the like. Generally the acid employed in this step is trifluoroacetic acid or acetic acid. The acid is typically added in a molar excess relative to vancomycin (and the base).

This acidification step is typically conducted at a temperature ranging from about 0° C. to about 30° C., preferably at about 25° C., for about 0.25 to about 2.0 hours, preferably for about 0.25 to about 1.5 hours.

Generally, a polar, protic solvent is added during this step, such as, by way of example, methanol, ethanol, propanol, isopropanol, butanol, ethylene glycol, and the like. Alternatively, a mixed polar protic/non-protic solvent may be used, such as methanol/tetrahydrofuran, methanol/1,2-dimethoxyethane and the like.

After the acidification step, the mixture is then contacted with a reducing agent to reduce the imine and/or hemiaminal. Any suitable reducing agent can be employed in this step of the process which is compatible with the functionality present in the glycopeptide. For example, suitable reducing agents include amine/borane complexes, such as sodium borohydride, sodium cyanoborohydride, zinc borohydride, sodium triacetoxyborohydride, pyridine/borane, tert-butylamine/borane, N-methylmorpholine/borane, ammonia/borane, dimethylamine/borane, triethylamine/borane, trimethylamine/borane, and the like.

Typically, the reduction (i.e., treatment with the reducing agent) is carried out in the presence of a protic solvent, such as, for example, an alcohol (e.g., methanol, ethanol, propanol, isopropanol, or butanol), water, or the like. Generally, a polar, protic solvent is present during this reduction step. The polar, protic solvent can have been added during the acidification step described above.

This reduction step of the process is typically conducted at a temperature ranging from about 0° C. to about 30° C., preferably at about 25° C., for about 0.5 to about 24 hours, preferably for about 1 to about 6 hours, or until the reduction is substantially complete.

If desired, the protecting group present on the n-decylaminoethyl side of the reductive alkylation product can be removed before the next step of the synthesis. For example, if a 9-fluorenylmethoxycarbonyl (Fmoc) protecting group is used, this group is typically removed by treatment with an amine, such as tert-butylamine. This reaction is generally conducted in the same reaction vessel as the reductive alkylation to afford N3"-[2-(decylamino)ethyl]vancomycin.

The glycopeptide derivative resulting from the reductive alkylation is then coupled with aminomethylphosphonic acid and formaldehyde at the resorcinol moiety under basic conditions to yield telavancin or a salt thereof. This step is typically conducted by contacting an excess of aminomethylphosphonic acid, such as about 2 to about 10 molar equivalents with about one molar equivalent of formaldehyde, such as about 0.9 to about 1.1 molar equivalents, and about one molar equivalent of the glycopeptide derivative resulting from the reductive alkylation or a salt thereof in the presence of a base.

The formaldehyde employed in this step of the process is typically added in an aqueous solution, for example, as a 37 wt. % solution in water optionally containing about 5 to about 15 wt. % methanol (i.e., Formalin).

Any suitable base may be used in this reaction including, for example, organic bases such as tertiary amines, and inorganic bases, such as alkali metal hydroxides (i.e., sodium hydroxide). Typically, the base is a tertiary amine such as, by way of example, triethylamine, diisopropylethylamine, and the like. The molar ratio of the base to the phosphono containing amine is about 3:1 to about 5:1. Typically, the pH of the mixture is about 10 to about 11. This reaction is conducted in an inert diluent, such as water, acetonitrile/water and the like. For example, this step of the process can be conducted in acetonitrile/water or water having a v/v ratio ranging from about 3:2 to completely water.

This step of the process is typically conducted at a temperature ranging from about −20° C. to about 30° C., for instance, from about −10° C. to about −5° C., for about 6 to about 48 hours, or until the reaction is substantially complete.

The resulting compound or salt is isolated by conventional procedures including, precipitation, filtration and the like. In a typical isolation procedure, the pH of the mixture is adjusted to between about 2 to about 3 by addition of a suitable acid, such as aqueous hydrochloric acid. Generally, the temperature of the mixture is maintained below about 5° C. during acidification. An organic diluent, such as acetonitrile is then added to promote precipitation of the reaction product and the resulting precipitate is collected by filtration and optionally washed with additional diluent. Alternatively, this solution may be used directly to form the hydrochloride salts of the present invention.

If desired, the precipitate formed above is further purified using reverse-phase HPLC or other chromatographic methods, such as, for example, resin chromatography. A wide variety of suitable polystyrene-divinyl benzene resins for use in resin chromatography are available commercially, such as, for example, from TosoHaas (Montgomery, Pa.), Rohm & Haas (Philadelphia, Pa.), Mitsubishi Chemical Industries LTD. (Tokyo, Japan); and Dow Chemical Co. (Midland, Mich.).

The resin is prepared by wetting in excess water and washing with acidified water and/or with an aqueous solution of a acidified polar organic solvent. The sample of telavancin to be purified is dissolved in acidified water optionally containing a polar organic solvent.

Suitable polar organic solvents include methanol, ethanol, isopropyl alcohol, acetonitrile, and the like. Suitable acids for the acidification of the first and second aqueous solutions include acetic acid, trifluoroacetic acid, hydrochloric acid, sulfuric acid, phosphoric acid and like acids. The pH of the sample solution is preferably between about 2 and about 5. A small portion of the sample solution is removed and used as a standard for analysis.

The sample solution is loaded onto the column and eluted with a second solution of an acidified polar organic solvent, which is collected from the column in fractions. Typically, the second acidified aqueous solution is at a concentration of about 10 mM acid and is proportionally in a ratio of from about 1:3 to about 1:15 polar organic solvent:water.

Each fraction is monitored for presence, concentration and purity of sample, for example, by thin layer chromatography or HPLC. The fractions containing a sample purity higher than a set threshold, such as by way of illustration, about 85% pure telavancin (or salt thereof), are pooled. Typically, the concentration of Compound 1 in the fractions to be pooled is about 0.5-5.0 mg/mL.

In order to increase the concentration of telavancin, the pooled fractions collected above are loaded onto a second polystyrene resin column. This procedure also serves as a salt exchange process to convert any secondary salts (formed by the interaction of the acid and telavancin during the purification step above) to hydrochloride salts. Typically telavancin is prepared as a hydrochloride salt. However, during the purification step described above, minute amounts of a different salt can be formed.

The pooled fractions collected during the earlier purification step are diluted with water, for example, the fractions can be diluted about two times, then loaded onto a second resin chromatography column. A solution of acetonitrile:water: hydrochloric acid, in a volume ratio of, for example, 10:90: 0.5, is used to wash the column. A solution of acetonitrile-water in a volume ratio of ~40-60:60-40 is used to elute the compound of interest from the column while the fractions are monitored. Fractions containing a sample concentration that is higher than a desired threshold, such as, for example, 5 mg/mL, are pooled. For further purification or concentration, this resin chromatography purification step can be repeated multiple times. Alternatively, the purified product can be isolated from the eluate by precipitation and filtration, or by other methods known to those in the art.

Typically, the resulting pooled fractions are a trihydrochloride salt of telavancin having a chloride ion content greater than 5.0 wt. % in an aqueous solution of acetonitrile with a pH of less than or equal to about 2.0.

For the process of the present invention described herein, the composition of step (a) can be the pooled fractions collected in the concentration and salt exchange step described above or the fractions can be further processed, such as dried or lyophilized, then redissolved in an aqueous solvent system to comprise the composition of step (a).

The methods employed in the above reactions are well-known in the art. Suitable reagents are either commercially available or can be prepared by conventional procedures using commercially available starting materials and conventional reagents. See, for example, *Advanced Organic Chemistry*, Jerry March, 4th ed., 1992, John Wiley and Sons, New York, page 959; and Frank R. Hartley (ed.) *The Chemistry of Organophosphorous Compounds*, vol. 1-4, John Wiley and Sons, New York (1996), and references cited therein.

Additional details and methods for preparing the compound of this invention are described in the Examples below.

The following examples are provided to illustrate this invention and are not to be construed in any way as limiting the scope of this invention.

EXAMPLES

In the Examples below, the following abbreviations have the following meanings. Any abbreviations not defined have their generally accepted meaning. Unless otherwise stated, all temperatures are in degrees Celsius (° C.).

ACN=acetonitrile
BV/h=bed volume per hour
DMF=N,N-dimethylformamide
eq.=molar equivalent
Fmoc=9-fluorenylmethoxycarbonyl
MTBE=methyl tert-butyl ether
TLC=thin layer chromatography
TFA=trifluoroacetic acid In the examples described below, HPLC sample analysis was conducted using an Agilent (Palo Alto, Calif.) Series 1100 instrument with Zorbax RP-Bonus 4.6 mm×250 mm columns, supplied by Agilent, having a 5 micron pore size, packed on C14 silica. Detection was by UV absorbance at 254 nm. Mobile phase A was 2%-98%-0.1% ACN-$H_2O$-TFA; and mobile phase B was 90%-10%-0.1% ACN-$H_2O$-TFA. A flow rate of 1.0 mL/min was used with moble phase A containing a gradient of mobile phase B as follows: 10 to 43% B for 30 min; 43% B for 5 min; 43 to 100% B for 5 min; 100 to 10% B for 1 min; and 10% B for 14 min.

In the following examples, vancomycin hydrochloride semi-hydrate was purchased from Alpharma, Inc. Fort Lee, N.J. 07024 (Alpharma AS, Oslo Norway). Other reagents and reactants are available from Aldrich Chemical Co., (Milwaukee, Wis.). Also, unless noted otherwise, reagents, starting materials and solvents were purchased from commercial suppliers (such as Aldrich, Fluka, Sigma and the like) and were used without further purification.

A Brinkmann Metrohm Karl Fischer Model 831 Coulometer with Model 703 pump/stirrer was used to determine the water content of the test samples. The weight percent of chloride ions in the test samples was determined by potentiometric titration using 0.1 N silver nitrate and a 736 GP Titrino Potentiometric Titrator, Metrohm Ltd. (Herisau, Switzerland). The equipment was calibrated regularly against known samples to verify accuracy.

Example 1

Synthesis of a Hydrochloride Salt of Telavancin Having a Chloride Ion Content of Greater than About 4.8 a. Preparation of $N^{van}$-2-(n-Decylamino)ethyl Vancomycin Hydrochloride

To a 5 L three-necked flask equipped with mechanical stirrer, a thermometer, and a nitrogen bubbler was added DMF (760 g, 800 mL), and warmed to 30-35° C. While stirring, 24 mL of diisopropylethylamine (18.1 g, 0.14 mol, 2 eq) and vancomycin hydrochloride (100 g, 0.067 mol, 1 eq) (in portions) were added successively. The addition funnel was rinsed with DMF (114 g, 120 mL). The mixture was stirred at 30-35° C. for 0.5 h, then cooled to 20-25° C. N-Fmoc-decylaminoacetaldehyde (29.7 g, 0.07 mol, 1.05 eq) was added to the mixture, which was stirred at 20-25° C. for 6-8 h. Methanol (220 g, 280 mL), followed by trifluoroacetic acid (31.2 g, 21 mL, 0.272 mol, 4 eq) were added. After the mixture was stirred for about 15 min, borane tert-butylamine complex (5.7 g, 0.067 mol, 1 eq) was added, and the mixture was stirred for about 2 h. Tert-butylamine (29.8 g, 0.403 mol, 6 eq) was added and the resulting mixture was warmed to about 55° C. and stirred for 2-3 h. The mixture was cooled to about 20-25° C. and 0.5 N HCl (540 mL) at about 20-25° C. was added to adjust the solution to pH 7.25~7.35. A 10% brine solution (2400 g) was added over approximately 4 h while the temperature was maintained at about 20-25° C., after which the suspension was cooled to 0-5° C. and was stirred for 3~4 h. The resulting slurry was filtered through Whatman #2 filter paper (18.5 cm diameter, 8 micron). The wet cake was washed successively with water (2×200 g) and methyl tert-butyl ether (2×200 g). The wet cake was re-slurried with ethyl acetate (600 g) for 8~12 h. This mixture was filtered, then washed with ethyl acetate (2×100 g). The wet cake was dried at 40° C. under house vacuum (40~50 mm Hg) until the water content reached a limit of detection (LOD) of less than about 10%. The title compound (102 g, ~85% purity) was obtained as an off-white powder and was used in the next reaction without purification.

b. Preparation of Crude Telavancin Hydrochloride

To a 12 L three-necked flask equipped with a mechanical stirrer, a thermometer, and a nitrogen bubbler was added aminomethylphosphonic acid (47.7 g, 0.43 mol, 5 eq). Acetonitrile (786 g, 1 L) and water (1000 g, 1 L) were added and the mixture was stirred to dissolve at 20-25° C. Diisopropylethylamine (222 g, 0.3 L, 20 eq) was added and the mixture was stirred at 20-25° C. for 20 min. The product of preparation (a) above, $N^{van}$-2-(n-Decylamino)ethyl vancomycin hydrochloride, (200 g, 0.086 mol assayed, 1 eq) was added, and the mixture was stirred at 20-25° C. for 1 h. The mixture was cooled to −5° C., before adding 37 wt. % formaldehyde in water (9.08 g, 0.111 mol, 1.3 eq). The mixture was stirred under nitrogen for 12-24 h. To the reaction mixture was added dropwise 3N HCl (615 mL) to adjust the pH of the mixture from 10.8 to 2.8. The mixture was warmed to 20-25° C. Ethanol (95%, 8 L) was added to the mixture over a period of ~2.5 h. The resulting suspension was stirred at 5-10° C. for 16 h. The suspension was filtered through a Whatman #2 filter paper (24 cm diameter, 8 micron). The wet cake was washed with ethyl acetate (2×200 mL) to give a fine off-white powder. The cake was dried at 25° C. to yield telavancin hydrochloride and confirmed as the title compound by HPLC analysis (184 g, 76.5% purity).

c. Purification Step

HP20SS polystyrene-divinyl benzene resin (Agilent) was loaded onto a 2"×25 cm column fitted with a back pressure regulator, a peristaltic pump, a UV detector, and a fraction collector.

The column was preconditioned by pumping 3 bed volume (BV) of 100% ethanol through the column at a flow rate of about 2-3 BV/h. The column was equilibrated with mobile phase A {15% ethanol (190 proof, denatured with 5% methanol), 85% water, 1% acetic acid} for 3-5 BV at a flow rate of 2-3 BV/h before sample loading.

A solution of the product from Preparation (b) above was mixed with 80:10:10 (v/v/v) water:ethanol:acetic acid at a concentration of 20-25 mg/mL and stirred for 1-2 h. The solution was mixed with Celite (5 g/L of solution) for 15 min, filtered through a 1 micron filter and loaded onto the column at 1.5 BV/h. The column was washed using mobile phase A at 20 mL/min for 30 min (~1 BV). Mobile phase B (26% ethanol, 72% water, 1% ethyl acetate, 1% acetic acid) at a flow rate of ~1 BV/h (13.5 mL/min for Biotage 75M cartridge) was used over ~5 h to elute separate fractions having a volume of approximately 27 mL each.

Each fraction was analyzed by thin layer chromatography for the presence of telavancin. Fractions containing telavancin were then analyzed by HPLC to determine the concentration and purity of telavancin in the fraction. Those fractions having a purity of at least 85% were pooled. The total volume of the pooled fractions with acceptable purity was ~5 BV.

d. Concentration and Salt Exchange

Amberlite XAD-1600 polystyrene-divinyl benzene resin (Rohm & Haas) was washed with a mixture of 90% deionized water, 10% ethanol, and 0.1% acetic acid (v/v/v) for 3 days. The resin was loaded into the column, then the column was preconditioned by pumping 3 bed volumes (BV) of 100% ethanol through the column at a flow rate of about 2 BV/h. The column was equilibrated with mobile phase A {15% ethanol (190 proof, denatured with 5% methanol), 85% water, 0.6% acetic acid} for 3-5 BV at a flow rate of ~2 BV/h before sample loading.

The pooled fractions collected in Purification Step (c) above were diluted with water (2× pooled fraction volume) and the solvent composition was adjusted from 25% aqueous ethanol to 85% water, 15% ethanol by adding water. The solution was then pumped onto the column at a flow rate of ~1 BV/h. The catch efficiency, monitored by UV detector, was determined to be >98%.

A solution of acetonitrile-water-conc. aqueous hydrochloric acid in a volume ratio of 10:90:0.5 was prepared and pumped onto the column for 2 BV at a flow rate of ~1 BV/h.

A solution of acetonitrile-water in 50:50 volume ratio, adjusted to pH 2.0 with concentrated HCl, was then pumped onto the column at a flow rate of ~1 BV/h to elute the hydrochloride salt of telavancin from the column.

Each fraction was collected and tested for the presence of the hydrochloride salt of telavancin. Fractions were collected until the hydrochloride salt of telavancin was no longer detected. Fractions that contained about 20-30% hydrochloride salt of telavancin were pooled. 2-3 BV of the release solution was enough to recover >95% of the captured sample. The pooled fractions were either used directly in the process described in Example 2 below, or were lyophilized and then redissolved for use in the process described in Example 2.

Example 2

Preparation and Isolation of a Hydrochloride Salt of Telavancin Having a Chloride Ion Content of 4.1 wt. %

A hydrochloride salt of telavancin (1.14 L) (prepared as described in Example 1) was dissolved in 1:1 (v/v) acetonitrile and water (pH 1.93, concentration ~30 mg/mL). The pH of the solution was adjusted to pH 3.78 with 10 N aqueous NaOH (~3 mL) at 22° C. To this solution was added dropwise acetonitrile (3.42 L) at 22° C. over a 3.5 h period to give a precipitate as a milky suspension. This mixture was stirred for 1.5 h and was allowed to stand without stirring for about 14 h. The precipitate mixture was then filtered and the resulting wet cake was washed successively with acetonitrile and MTBE (200 mL each). The wet cake was dried under nitrogen for 1 h, then sieved (500 micron). The resulting powder was dried at 22° C. under a 45-50 mm Hg vacuum for 96 h to give 32.5 g (~40%) of the title compound as an off-white powder. (HPLC purity 91.3%, 3.84 wt. % chloride, 5.84 wt. % water). This material had a chloride ion content of 4.1 wt. % after adjustment for the water content.

Using the process described above and by varying the amount of NaOH added, hydrochloride salts of telavancin having a chloride ion content of 5.74, 5.60, 4.69, 4.59, 4.41, 3.94, 3.68, and 2.42 wt. % were isolated from solutions having a pH of 1.8, 2.0, 2.5, 3.0, 3.5, 4.0, 4.5, and 5.0, respectively.

Example 3

The Effect of Chloride Ion Content on Stability

The effect of chloride ion content on the stability of hydrochloride salts of telavancin stored at −20° C., 5° C. and 25° C. was determined.

Eight lots of telavancin hydrochloride salts prepared as described in Example 2 were placed in identical glass vials and stored at −20° C., 5° C. and 25° C. under otherwise identical conditions for two weeks. The changes in HPLC area % for the pseudoaglycone and aglycone impurities were used to evaluate relative stability.

Results for samples stored at the highest temperature, 25° C., are displayed below in Table 1. The increase in pseudoaglycone and aglycone impurities for samples stored at the lower temperatures was smaller in magnitude but demonstrated the same trends.

TABLE 1

Experimental Data of Hydrochloride Salts of Telavancin Stored at 25° C. Over a 2-Week Period

| pH | Cmpd 1 Chloride Ion Content (%) | Pseudoaglycone of Cmpd 1 (HPLC area %) | | | Aglycone of Cmpd 1 (HPLC area %) | | |
|---|---|---|---|---|---|---|---|
| | | Initial | 2 Week | 2-Week Change | Initial | 2 Week | 2-Week Change |
| 1.8 | 5.74 | 0.89 | 1.94 | +1.05 | 0.43 | 1.08 | +0.65 |
| 2.0 | 5.60 | 0.48 | 1.11 | +0.63 | 0.15 | 0.41 | +0.26 |
| 2.5 | 4.69 | 0.45 | 0.62 | +0.17 | 0.07 | 0.13 | +0.06 |
| 3.0 | 4.59 | 0.52 | 0.72 | +0.20 | 0.10 | 0.17 | +0.07 |
| 3.5 | 4.41 | 0.42 | 0.53 | +0.11 | 0.06 | nd* | nd* |
| 4.0 | 3.94 | 0.43 | 0.56 | +0.13 | 0.04 | 0.09 | +0.05 |
| 4.5 | 3.68 | 0.43 | 0.51 | +0.08 | 0.06 | 0.08 | +0.02 |
| 5.0 | 2.42 | 0.32 | 0.40 | +0.08 | 0.03 | 0.05 | +0.02 |

*not determined.

The chloride ion content displayed in Table 1 was calculated with the water content of the sample deducted. For each sample, the pH of the mixture from which it was isolated, is indicated. The column entitled, "2 Week Change" is the difference in HPLC area % between the value observed after two weeks and the initial value and is graphically illustrated in FIGS. 1 and 2.

Figure 2:
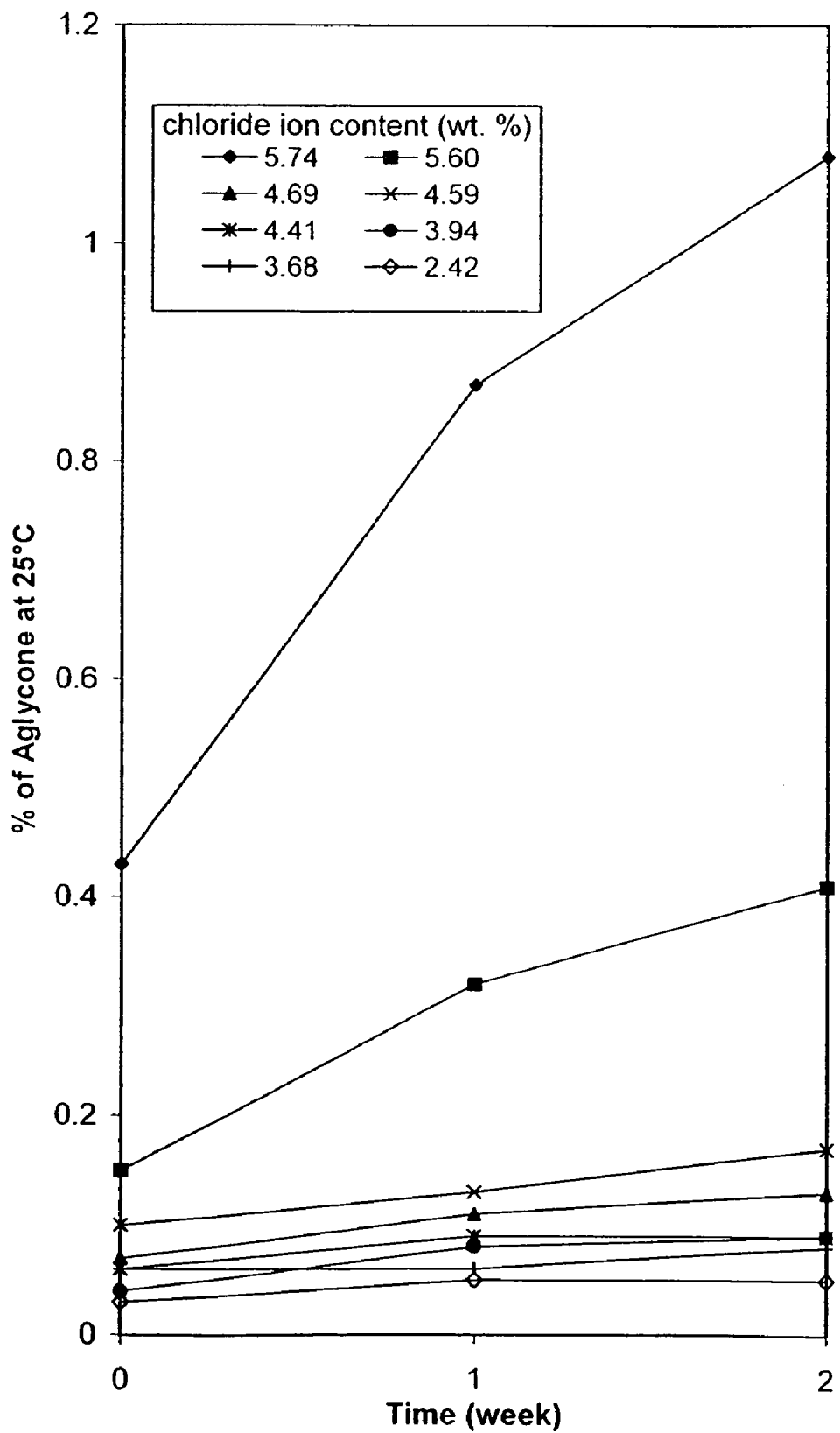
FIG. 2 is a graph showing the HPLC area percent of aglycone present in eight samples of hydrochloride salts of telavancin vs. time when the samples are stored at 25° C.

As shown in FIGS. 1 and 2, hydrochloride salts of telavancin having a chloride ion content of greater than 4.8 wt. % (5.74 wt. % and 5.60 wt. %), i.e., those precipitated at low pH conditions (pH 1.8 and 2.0) had increased levels of hydrolyzed byproducts over a two week period at 25° C. Specifically, after two weeks, hydrochloride salts of telavancin precipitated at low pH had an increase in the HPLC area % for the pseudoaglycone impurity of 0.6 or greater; and an increase in the HPLC area % for the aglycone impurity of 0.3 or greater.

Surprisingly, hydrochloride salts of telavancin having a chloride ion content of from about 2.4 wt. % to about 4.8 wt. % were notably more stable under the same conditions. For such salts, the 2-week change in HPLC area % for the pseudoaglycone impurity ranged between 0.1 and 0.2. Similarly, the change in HPLC area % for the aglycone impurity was less than 0.1. Accordingly, the hydrochloride salts of the present invention showed significantly improved stability compared to previously disclosed salts.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A process for preparing a hydrochloride salt of telavancin; the process comprising:
   (a) forming an aqueous composition comprising a hydrochloride salt of telavancin, wherein the aqueous composition has a pH of about 3.5 to about 4.5;
   (b) adding an organic diluent to the aqueous composition of step (a) to precipitate the hydrochloride salt of telavancin; and
   (c) filtering the aqueous composition of step (b) to provide the hydrochloride salt of telavancin.

2. The process of claim 1, wherein the aqueous composition has a pH of about 3.5 to about 4.0.

3. The process of claim 1 or 2, wherein the organic diluent is acetonitrile.

4. The process of claim 1 or 2, wherein the organic diluent is acetone.

5. The process of claim 1 or 2, wherein the process further comprises:
   (d) washing the hydrochloride salt of telavancin from step (c) with methyl tert-butyl ether.

* * * * *

UNITED STATES PATENT AND TRADEMARK OFFICE
CERTIFICATE OF CORRECTION

| | | |
|---|---|---|
| PATENT NO. | : 8,003,755 B2 | Page 1 of 1 |
| APPLICATION NO. | : 12/082096 | |
| DATED | : August 23, 2011 | |
| INVENTOR(S) | : Jyanwei Liu et al. | |

It is certified that error appears in the above-identified patent and that said Letters Patent is hereby corrected as shown below:

On the Title Page, Item (73) under Assignee:

"Thervance, Inc." should read "Theravance, Inc.".

Signed and Sealed this
Twenty-ninth Day of May, 2012

David J. Kappos
*Director of the United States Patent and Trademark Office*